(12) United States Patent
Fukui

(10) Patent No.: US 7,843,555 B2
(45) Date of Patent: Nov. 30, 2010

(54) THERMOPLASTIC PLASTIC AND METHOD FOR PRODUCING THE SAME

(75) Inventor: Shinya Fukui, Toyonaka (JP)

(73) Assignee: Plagenom Co., Ltd., Osaka-Shi (JP)

( * ) Notice: Subject to any disclaimer, the term of this patent is extended or adjusted under 35 U.S.C. 154(b) by 1056 days.

(21) Appl. No.: 11/596,060

(22) PCT Filed: May 10, 2005

(86) PCT No.: PCT/JP2005/008498

§ 371 (c)(1),
(2), (4) Date: Nov. 9, 2006

(87) PCT Pub. No.: WO2005/108474

PCT Pub. Date: Nov. 17, 2005

(65) Prior Publication Data

US 2007/0268734 A1 Nov. 22, 2007

(30) Foreign Application Priority Data

May 10, 2004 (JP) .............................. 2004-139652

(51) Int. Cl.
*G01N 21/00* (2006.01)

(52) U.S. Cl. ....................................................... 356/72

(58) Field of Classification Search .................. 356/111; 264/21; 235/491
See application file for complete search history.

(56) References Cited

U.S. PATENT DOCUMENTS

| 6,246,061 B1 * | 6/2001 | Ramsey et al. ........... 250/458.1 |
| 6,673,437 B2 * | 1/2004 | Kohla et al. .................. 428/332 |

FOREIGN PATENT DOCUMENTS

| JP | 2002-332414 | 11/2002 |
| JP | 2002-336798 | 11/2002 |

* cited by examiner

*Primary Examiner*—Tarifur Chowdhury
*Assistant Examiner*—Abdullahi Nur
(74) *Attorney, Agent, or Firm*—Kratz, Quintos & Hanson, LLP

(57) ABSTRACT

A method for producing thermoplastic plastic capable of grasping information concerning the production process even after distribution. In a plurality of production processes including fusion of thermoplastic plastic 90, an information presenting substance 91 is added to the thermoplastic plastic sequentially and dispersed therein in each of the production process, wherein the information presenting substance is associated with information concerning each of the production process and radiates fluorescence upon an irradiation of an electromagnetic wave in a specified wavelength region.

13 Claims, 4 Drawing Sheets

THERMOPLASTIC PLASTIC AND METHOD FOR PRODUCING THE SAME

TECHNICAL FIELD

The present invention relates to a thermoplastic plastic and a method for producing the same.

BACKGROUND ART

In general, as a method for displaying information such as a product name, a manufacture-maker name, and a lot mark of a plastic product or the like, a method such as a method for describing the information on a label appended to the product, or a method for directly incusing the information on the product, is included.

Meanwhile, methods for reading out information associated with the kind etc. of an information presenting substance in advance, by adding an information presenting substance to various kinds of target objects in advance and detecting fluorescence radiated by the information presenting substance (see; Japanese Unexamined Patent Publication Nos. 2002-332414 and 2002-336798) have been suggested.

DISCLOSURE OF THE INVENTION

Problems to be Solved by the Invention

Although, in recent years, in some cases, for a purpose such as search for cause when a problem in quality is occurred, separation for recycling, and determination whether the product is genuine product or not, it is required to specify the composition and the production history or the like of each product, in many cases, it is insufficient to achieve such a purpose by merely using information described in a known general labeling etc.

Specifically, since, in general, a thermoplastic plastic goes through a plurality of makers from the production of a raw material plastic to the production of a plastic product, and information concerning the production process such as information of the base material of the plastic, or information of the type and the composition of an additive exists with being distributed in respective makers involved directly or indirectly in the production, there have been a problem that such information concerning the production process could not be sufficiently grasped.

Moreover, even in the above-mentioned known technology using an information presenting substance, there has been room for improvement in view of grasping information concerning the production process.

The present invention is performed in view of the above-mentioned problems, and the object of the present invention is to provide a thermoplastic plastic capable of grasping information etc. concerning the production process, and a method for producing the same.

Means to Solve the Problems

The present invention provides the following means.

[1] A method for producing a thermoplastic plastic comprising a plurality of production processes including fusion of the thermoplastic plastic and an information presenting substance is added to the thermoplastic plastic sequentially and dispersed therein in each of the production process, wherein the information presenting substance is associated with information concerning each of the production process and radiates fluorescence upon an irradiation of an electromagnetic wave in a specified wavelength region.

[2] The method for producing a thermoplastic plastic as recited in the aforementioned Item [1], wherein the plurality of production processes including fusion of the thermoplastic plastic are performed with being shared by a plurality of producers.

[3] The method for producing a thermoplastic plastic as recited in the aforementioned Item [1] or [2], wherein the information presenting substance is an inorganic compound including lanthanoid elements.

[4] The method for producing a thermoplastic plastic as recited in any one of the aforementioned Items [1] to [3], wherein the information concerning each of the production process associated with the information presenting substance includes at least any one of information concerning a base material of the thermoplastic plastic, information concerning additives in each of the production process, information concerning producers performing each of the production process and information concerning a product obtained from the thermoplastic plastic.

[5] A thermoplastic plastic to which an information presenting substance is added sequentially and dispersed therein in each of a plurality of production processes including fusion of the thermoplastic plastic, wherein the information presenting substance is associated with information concerning each of the production process and radiates fluorescence upon an irradiation of an electromagnetic wave in a specified wavelength region.

[6] An information management device of a thermoplastic plastic for managing information concerning a plurality of production processes including fusion of the thermoplastic plastic, wherein the device associates information concerning each of the production process with information concerning information presenting substance which is added to the thermoplastic plastic and dispersed therein in each of the production process and radiates fluorescence upon an irradiation of an electromagnetic wave in a specified wavelength region and memorizes them.

[7] The information management device of a thermoplastic plastic as recited in the aforementioned Item [6], wherein information specifying information presenting substances to be added in each of the production process is sent to a terminal used by a producer performing each of the production process through network circuit.

[8] The information management device of a thermoplastic plastic as recited in the aforementioned Item [6] or [7], wherein the device obtains information concerning fluorescence spectrum as information concerning the information presenting substance from a detector for detecting the fluorescence spectrum and outputs information concerning each of the production process of the thermoplastic plastic associated with the information concerning the information presenting substance, and wherein the detector irradiates a predetermined electromagnetic wave to the thermoplastic plastic and detects the fluorescence spectrum radiated by the information presenting substance.

EFFECT OF THE INVENTION

According to the method for producing a thermoplastic plastic as recited in the above-mentioned invention [1], since an information presenting substance is added to the thermoplastic plastic sequentially and dispersed therein in each of a plurality of production processes including fusion of thermoplastic plastic and the information presenting substance is associated with information concerning each of the production process and radiates fluorescence upon an irradiation of an electromagnetic wave in a specified wavelength region, it is possible to incorporate the information concerning the production process in the thermoplastic plastic itself distributed as a material or a molded product so as to grasp information concerning the production process easily even after the thermoplastic plastic is distributed.

According to the above-mentioned invention [2], it is possible to grasp information concerning each of the production process easily even after the thermoplastic plastic is distributed by incorporating the information concerning the plurality of production processes performed with being shared by a plurality of producers, in the thermoplastic plastic itself.

According to the above-mentioned invention [3], since the information presenting substance is an inorganic compound including lanthanoid elements, the information presenting substance is not modified even under a high temperature due to fusion, thus enabling to carry the information concerning the production process.

According to the above-mentioned invention [4], it is possible to grasp the information concerning the base material of the thermoplastic plastic, the information concerning the additives in each of production process, the information concerning the producers performing each of production process or the information concerning the products obtained from the thermoplastic plastic so as to use it respective purposes such as recycling.

According to the thermoplastic plastic as recited in the above-mentioned invention [5], since an information presenting substance is added to the thermoplastic plastic sequentially and dispersed therein in each of a plurality of production processes including fusion of the thermoplastic plastic and the information presenting substance is associated with information concerning each of the production process and radiates fluorescence upon an irradiation of an electromagnetic wave in a specified wavelength region, it is possible to incorporate the information concerning the production process in the thermoplastic plastic itself distributed as a material or a molded product so as to grasp the information concerning the production process easily even after the thermoplastic plastic is distributed.

According to the information management device as recited in the above-mentioned invention [6], since the device associates the information concerning each of the production process of the thermoplastic plastic with the information concerning the information presenting substance added to the thermoplastic plastic in each of the production process and memorizes them, the information concerning the production process and the information concerning the information presenting substance can be managed in an integrated manner. This enables to easily grasp the information concerning the production process even after the thermoplastic plastic is distributed and to enhance the confidentiality of the information concerning the information presenting substance, thereby resulting in reduction of possibility of false products.

According to the above-mentioned invention [7], since the information specifying the information presenting substance to be added in each of the production process is sent from the information management device to a terminal used by a producer, a rule associating the information concerning the production process and the information concerning the information presenting substance can be managed in an integrated manner in the information management device.

According to the above-mentioned invention [8], since the information management device outputs the information concerning each of the production process of the thermoplastic plastic depending on the information concerning the fluorescent spectrum obtained by the detector from the thermoplastic plastic, it is possible to manage the information concerning the information presenting substance only by a side of the information management device without having a side of each detector memorize it so that the confidentiality of the information concerning the information presenting substance is further enhanced, and the possibility of false products is reduced.

DESCRIPTION OF REFERENCE NUMERALS

Figure 1:
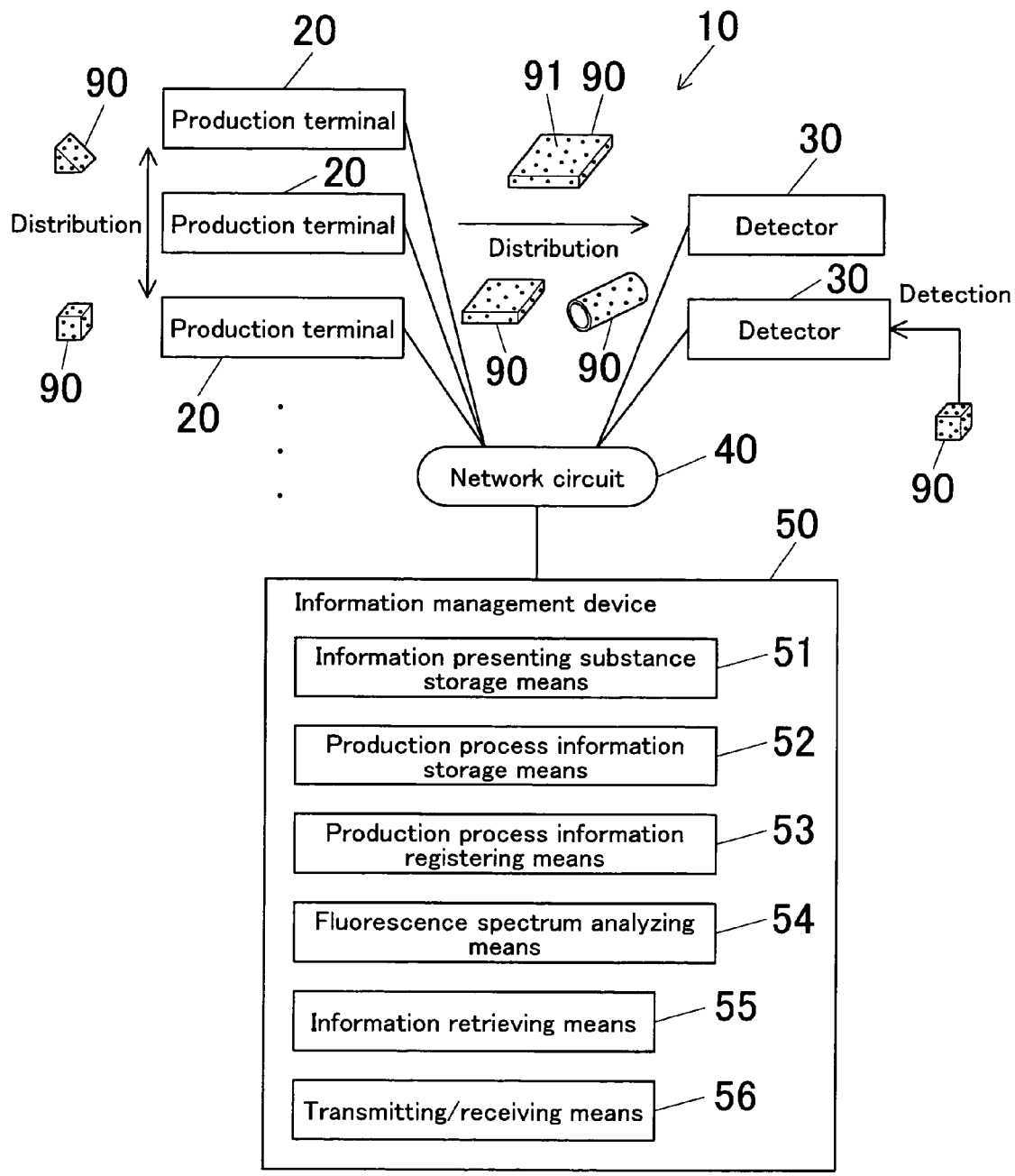
FIG. 1 is an entire configuration view of an information management system.

10 Information management system
20 Producer terminal
30 Detector
40 Network circuit
50 Information management device
51 Information presenting substance storage means
52 Production process information storage means
53 Production-process-information registering means
54 Fluorescence-spectrum analyzing means
55 Information retrieving means
56 Transmitting/receiving means
90 Thermoplastic plastic
91 Information presenting substance

BEST MODE FOR CARRYING OUT THE INVENTION

Next, embodiments of the present invention will be described.

In the present invention, in respective production processes generally performed with being shared by respective special makers, using a characteristic of a thermoplastic plastic that the thermoplastic plastic can be subjected to melting by heating and solidifying by cooling repeatedly, by adding an information presenting substance associated with the information concerning respective production processes to the material of a thermoplastic plastic itself and a final product itself using the material, information concerning the production process is incorporated in the material of the thermoplastic plastic itself and the final product itself using the material.

<Thermoplastic Plastic>

As for the type of a thermoplastic plastic to be a target object in which such information concerning the production process, it is not specifically limited, rather those which can be subjected to a multiple times of melting by heating and solidifying by cooling may be used. Specifically, various types of thermoplastic plastics using polyethylene, polypropyrene, polyamide, polyacetal, saturated polyester, fluororesin, vinyl chloride resin, polystyrene, methacrylic resin, polycarbonate, polyphenylene oxide, polysulfone, polyphenylene sulfide, methylpentene resin, and the like, as a base material, can be a target object. Moreover, those which is added various types of additives such as a filler, a reinforcer, and a stabilizer, may also be included.

Moreover, in the present specification, it is not limited for the thermoplastic plastic which is subjected to a predetermined molding as an entire or a part of a final product, rather a material itself distributed in production stages, before subjected to molding as the final product, is also included.

Specifically, as for the type of a specific final product, it is also not limited in particular, however, for example, various types of products distributed in a market which constitute home electric appliances, accessories for a dress, clothing accessories, bags, shoes, accessories, clocks, finger rings, clothes, stationeries, devices for eating, interior products and the like, can be included. Moreover the final products may be deeds, corporation securities, certificates, bank bills, coins, passports, driver's licenses, health insurance cards, checks, or capital stock certificates etc., which are distributed or delivered and received under a public trust or a given confidential relationship in general society. Moreover, the final products may be envelopes for products etc. (such as inner boxes, outer boxes, accounts, cartridge papers, and cartridge bags), and labels and tags appended to products etc.

<Production Process>

In general, such a thermoplastic plastic is produced via a plurality of production processes including fusion. As processes including fusion, specifically, processes such as (1) a polymerization process of the thermoplastic plastic, (2) a production process of a granulated body of the thermoplastic plastic, (3) a production process of an additive concentrated composition, (4) a production process of a composition of the thermoplastic plastic, (5) a molding process of a thermoplastic-plastic product, and (6) a secondary molding process of the thermoplastic-plastic product are included.

In general, such a plurality of production processes including fusion are often performed with being shared by a plurality of producers (makers). In such a case, since the information concerning the production processes is scattered in respective producers, there is a situation that it is difficult to grasp respective pieces of information in an ex-post manner.

Moreover, the thermoplastic plastic according to the present invention is not limited to those passed through all of the above-mentioned production processes, rather the above-mentioned production processes are examples.

Moreover, even when the thermoplastic plastic is produced via a plurality of production processes including fusion, it is not always required to add information presenting substances associated with information concerning the production process to the thermoplastic plastic in all of the production processes.

<Information Concerning Production Process>

As information concerning such production processes, which is present in a thermoplastic plastic by being associated with an information presenting substance to be added to the thermoplastic plastic, information such as information concerning the base material of the thermoplastic plastic, information concerning the additives in respective production processes, information concerning manufactures performing respective production processes, information concerning applications of the thermoplastic plastic, and information of production date, production method, and conditions such as a controlling temperature in respective production processes, can be included. In addition, the information concerning production processes associated with the information presenting substance is not limited to these pieces of information.

As the information concerning the base material of the thermoplastic plastic, type, ratio, degree of polymerization and the quality information etc. of monomers, can be included.

As the information concerning the additives, information such as type, composition, addition quantity and particle diameter of the additives and further part number specifying the additives, can be included.

As the information concerning producers performing respective production processes, identifying information etc. which can specify a matter such as the name of the producer, the production place (nation or country), the producing facility, and the producing line, can be included.

As the information concerning the application of the thermoplastic plastic, information of the type of a final product such as a base board for a credit card, an automotive part, or a part for electric appliance, in which the thermoplastic plastic is incorporated, information for specifying an intended purpose of the thermoplastic plastic in a final product such as a bumper, handle and the like, or for specifying buyers of them, can be included.

<Information Presenting Substance>

An information presenting substance contains a substance including one element or two or more elements, a compound of two or more elements, or a substance containing these elements or compound radiating a predetermined fluorescence when they are irradiated with an electromagnetic wave in a specified wavelength region (for example an ultraviolet light in a predetermined wavelength region). The fluorescence is radiated by the excitation of ions in the information presenting substance from a ground state to a higher energy level when the information presenting substance is externally irradiated, and by the following transition of the ions to a lower energy level. The information presenting substance radiates a fluorescent spectrum distribution specific to the type of itself.

It is preferable for the information presenting substance to include elements or compounds (oxides, sulfides, organic complexes, or the like) which are not contained in general in a various types of thermoplastic plastics. As the elements which are not contained in general in a various types of thermoplastic plastics, elements having atomic numbers 31 to 88, preferably lanthanoids, and more preferably, cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), and ytterbium (Yb) can be included.

Since these elements are easily measured by means of spectrum analysys, and further they are economical and not bad for health and easily available as oxides, one of these elements or combination of two or more of these elements are suitable as the information presenting substance. In addition, as for information presenting substances having same element, if they have another different type of element to be combined, or different combination ratios, they can be treated as another information presenting substances.

Moreover, when fluorescence from infrared light to ultraviolet light is used, a single crystal added with a transition element having an imperfect 3d shell and/or an imperfect 4f shell, glass added with a transition element having an imperfect 3d shell and/or an imperfect 4f shell, and a complex using a transition element having an imperfect 3d shell and/or an imperfect 4f shell as the center thereof, are suitable as the information presenting substance, because they can obtain high fluorescence intensity.

Moreover, as for the information presenting substance, it may be a predetermined mother substance added with a transition element, like yttrium oxide ($Y_2O_3$) containing europium ($Eu^{3+}$). As the mother substance, sulfide, nitride, hydroxide, halide, and a mixed crystal, are included, and further an amorphous substance and glass, etc., are also included. For example, such a substance which includes a transition element in the form of the chemical bond like a chelate compound, in which another atom or ion constituting a crystalline lattice is replaced, which is interrupted and included in a crystalline lattice, or which is contained in a crevice in glass, is included.

Especially, when the information presenting substance is produced using an inorganic oxide as the mother substance, it becomes very stable, and for example, even when it is exposed to a high temperature of 1000° C., it is not destroyed, rather remains in the target object. Therefore, even when the target object is subjected to incineration disposal, and further it is disposed illegally after incineration, the fluorescence of the information presenting substance can be detected. Moreover, even when the target object contains liquid, such as solution of an aqueous solvent or an organic solvent, or clouded color liquid, the information presenting substance can detect the fluorescence of the information presenting substance without receiving a chemical change.

Moreover, the information presenting substance is preferable to be fine particles having average particle diameter of 1 nm to 50 µm, preferably 10 nm to 10 µm, more preferably 50 nm to 10 µm, and the fine particles may form a polymer such as a dimer or a trimer. In this manner, by causing the particle diameter of the information presenting substance to be small, the change of the fluorescence of the information presenting substance by the difference in production histories tends to occur. For this reason, it is possible to enhance the confidentiality of the genuine information presenting substance by substantially increasing the variety of the information presenting substances. In order to make such fine particulates, various processes, such as a chemical reaction process, a sol gel process, a colloid process, a gas solidifying process, a gas reaction process, an evaporating-in gas process, a sputtering process, a glass crystallization process, a sedimentation process, and a spraying process, can be used.

Moreover, as the information presenting substance, a substance of which surface is modified by a surface modifying agent such as deuterium or an organic substance, and a substance of which periphery is covered with a substance other than the mother material, may be used. If such an information presenting substance is used, the particle diameter and the structure thereof can be stabilized, and the luminous efficiency thereof can be improved, and the information presenting substance tends to solve in a specific solvent, and can become conformable with the surrounding substance.

<Addition of Information Presenting Substance>

Addition of such an information presenting substance to the thermoplastic plastic is performed in each of the above-mentioned production processes including fusion and the information presenting substance is dispersed in the thermoplastic plastic.

Specifically, processes such as a process of directly molding the thermoplastic plastic after subjecting it to dry blending using a drum tumbler, a process of subjecting it to compound processing using an extruder, and a process of subjecting it to compound processing or molding using an internal mixer or a heating roller are included. Moreover, the addition after forming a master batch may be sufficient.

In addition, in order to secure uniform distribution and dispersion of the information presenting substance within the thermoplastic plastic to be a target object, fatty acid amide, fatty acid metal salt, or fatty acid ester, may be used as lubricant.

Moreover, the quantity of the information presenting substance added to the thermoplastic plastic is preferable to be within a small range which does not have influence on the appearance or physical properties according to the application of the thermoplastic plastic. Specifically, although variously changed according to the type etc. of the thermoplastic plastic, the range of 0.1 ppm or more and 1000 ppm or less is preferable with respect to the thermoplastic plastic. If the quantity is 0.1 ppm or more, the fluorescence presented by the information presenting substance can be surely detected, and if the quantity is 1000 ppm or less, the appearance or physical properties will not be affected in much thermoplastic plastics. Further, if the quantity is 0.5 ppm or more, the reliability of measurement concerning the detection of the fluorescence presented by the information presenting substance can be sufficiently secured. Moreover, if the quantity is 200 ppm or less, the appearance or physical properties will not be affected in much thermoplastic plastics, and the economic burden of adding the information presenting substance to the thermoplastic plastic can also be suppressed.

<Approaches for Associating Information Presenting Substance with Information Concerning the Production Process>

As for approaches for associating such an information presenting substance with the information concerning the production process, they are not limited in particular; if they are approaches that can specify the information concerning the production process from the information concerning the information presenting substance that can be read out from the produced thermoplastic plastic. As for the information concerning the information presenting substance which can be read out from the thermoplastic plastic, the type of the information presenting substance, the quantity of addition of each information presenting substance, the combination of a plurality of information presenting substances, the relative ratio (compounding ratio) between the plurality of information presenting substances or the like, may be included. The type and the quantity of addition of these information presenting substances can be specified from the spectrum of the fluorescence radiated by the information presenting substance when it is irradiated with an electromagnetic wave in a specified wavelength region, i.e., the wavelength and the intensity of the fluorescence.

Hereinafter, a specific example for adding sequentially the information presenting substances in respective production processes, will be described.

In this example, a case is assumed, where a total of five companies, a resin maker A company, a resin maker B company, a master batch manufacture maker C company, a master batch manufacture maker D company, and a molding processing maker E company, share the production processes including fusion, respectively, and produce various types of thermoplastic-plastic products.

Specifically, the resin makers A company and B company produce the base material of the thermoplastic plastics shown in the right columns of Tables 1 and 2, respectively, and add and disperse the information presenting substance that is the type and has the quantity in each left column to and in the thermoplastic plastic (here base substance) in a granulating process after resin synthesis.

TABLE 1

| Information presenting substance a | Information |
|---|---|
| 20 ppm | PP-based resin (product name: XXX), grade #1001 |
| 50 ppm | PP-based resin (product name: XXX), grade #1002 |
| ... | ... |

TABLE 2

| Information presenting substance b | Information |
|---|---|
| 20 ppm | LLDPE-based resin (product name: YYY), grade #2001 |
| 50 ppm | LLDPE-based resin (product name: YYY), grade #2002 |
| ... | ... |

As for the information concerning the production processes by these resin makers A company and B company, in this example, it is information for specifying the type of the thermoplastic plastic shown in right columns of Tables 1 and 2, including the part number of the base material of the thermoplastic plastic and information for specifying the producer (here A company or B company). The information concerning this production process is associated with the type and quantity of an information presenting substances added to each plastic, and memorized and stored in a predetermined information management device.

The master batch manufacture makers C company and D company produce the master batches shown in the right columns of Tables 3 and 4, respectively, and in respective production processes, the information presenting substances which are the types and have the quantities shown in each left column are added and dispersed to and in thermoplastic plastics (here the master batches).

TABLE 3

| Information presenting substance | | |
|---|---|---|
| c | d | Information |
| 100 ppm | 100 ppm | Master batch #PP10 |
| 100 ppm | 300 ppm | Master batch #PP20 |

TABLE 4

| Information presenting substance | | |
|---|---|---|
| e | f | Information |
| 100 ppm | 50 ppm | Master batch #310 |
| 100 ppm | 100 ppm | Master batch #320 |
| ... | ... | ... |

As for the information concerning the production processes by these master batch manufacture makers C company and D company, in this example, it is information for specifying the types of the master batches shown in right columns of Tables 3 and 4, including the part number of the master batches and information for specifying the producers (here C company or D company). The information concerning this production process is associated with the types and quantities of information presenting substances added to each plastic, and memorized and stored in the predetermined information management device.

In addition, in the information specifying the types of the master batches, the information concerning compounding compositions of each master batch shown in Tables 5 and 6, is included, and the information concerning the compounding compositions of each master batch is also memorized and stored in the predetermined information management device.

TABLE 5

| Master batch product name | Composition | |
|---|---|---|
| Master batch #PP10 | Resin XXX #1001 | 80 wt % |
| | Antioxidant AO1 | 10 wt % |
| | Lubricant | 5 wt % |
| | Colorant black | 5 wt % |
| Master batch #PP20 | Resin XXX #1001 | 75 wt % |
| | Antioxidant AO1 | 10 wt % |
| | Ultraviolet absorbers SS | 5 wt % |
| | Lubricant | 5 wt % |
| | Colorant Red | 5 wt % |

TABLE 6

| Master batch product name | Composition | |
|---|---|---|
| Master batch #310 | Resin YYY #2001 | 50 wt % |
| | Filler | 40 wt % |
| | Colorant black | 5 wt % |
| Master batch #310 | Resin YYY #2002 | 50 wt % |
| | Filler | 50 wt % |

When calculation is performed, including the above-mentioned information presenting substances (Tables 1 and 2) added by the resin manufacture makers A company and B company, and the above-mentioned information presenting substances (Tables 3 and 4) added by the master batch manufacture makers C company and D company, this indicates that the information presenting substances shown in the following Tables 7 and 8 are added and dispersed to and in each master batch having the compounding compositions in Tables 5 and 6.

TABLE 7

| Master batch | a | b | c |
|---|---|---|---|
| #PP10 | 16 | 100 | 100 |
| #PP20 | 15 | 100 | 300 |

TABLE 8

| Master batch | b | e | f |
|---|---|---|---|
| #310 | 10 | 100 | 50 |
| #320 | 25 | 100 | 100 |

The molding and processing maker E company produces the molded products shown in the right columns of Table 9, and, in the production process, the information presenting substances which are the types and have the quantities shown in the left columns of Table 9, are added and dispersed to and in thermoplastic plastics (here, molded products).

TABLE 9

| Information presenting substance | | | Information | | |
|---|---|---|---|---|---|
| g | h | i | | | |
| 10 ppm | 50 ppm | — | Molded product #S10 | For S company | Application ○○ |
| 50 ppm | 50 ppm | — | Molded product #T10 | For T company | Application ○○ |
| 10 ppm | — | 40 ppm | Molded product #V100 | For V company | Application ΔΔ |
| 10 ppm | — | 80 ppm | Molded product #W150 | For W company | Application □□ |

As for the information concerning the production process by the molding and processing maker E company, in this example, it is information for specifying the types of the molded products shown in right columns of Table 9, including the part numbers of the molded products and information for specifying the producer (here, E company). The information concerning this production process is associated with the types and the quantities of information presenting substances added to the molded products, and memorized and stored in the predetermined information management device.

In addition, in the information specifying the types of the molded products, the information concerning compounding compositions of each molded product shown in Table 10, is included, and the information concerning the compounding compositions of each molded product is also memorized and stored in the predetermined information management device.

TABLE 10

| Product name | Composition of the product | |
|---|---|---|
| Molded product #S10 | PP-based resin XXX #1001 | 70 wt % |
| | Polyolefine-based elastomer | 20 wt % |
| | Batch-master-batch #PP10 | 10 wt % |
| Molded product #T10 | PP-based resin XXX #1001 | 70 wt % |
| | Polyolefine-based elastomer | 20 wt % |
| | Batch-master-batch #PP10 | 10 wt % |
| Molded product #V100 | LLDPE-based resin YYY #2001 | 60 wt % |
| | Master batch #310 | 40 wt % |
| Molded product #W150 | PP-based resin XXX #1002 | 90 wt % |
| | Master batch #PP20 | 10 wt % |

When calculation is performed, including the above-mentioned information presenting substances (Tables 1 and 2) added by the resin manufacture makers A company and B company, which produce the main resin component, and the calculation results (Tables 7 and 8) of the type and the quantity of the information presenting substance added by the above-mentioned master batch, this indicates that the information presenting substances shown in the following Table 11 are added and dispersed to and in each molded product having the compounding compositions in Table 10.

TABLE 11

| Product name | a | b | c | d | e | f | g | h | i |
|---|---|---|---|---|---|---|---|---|---|
| Molded product #S10 | 15.6 | | 10 | 10 | | | 10 | 50 | |
| Molded product #T10 | 15.6 | | 10 | 10 | | | 50 | 50 | |
| Molded product #V100 | | 16 | | | 40 | 20 | 10 | | 40 |
| Molded product #W150 | 46.5 | | 10 | 30 | | | 10 | | 80 |

Moreover, in the predetermined information management device, each information presenting substance added in respective production processes, is memorized as information concerning the spectrum of the fluorescence radiated by the information presenting substance when it is irradiated with an electromagnetic wave in a specified wavelength region.

Moreover, the predetermined information management device has an analyzing function of analyzing the type and the quantity of an information presenting substance added and dispersed to and in the thermoplastic plastic, based on the information concerning the fluorescence spectrum detected from the thermoplastic plastic by the predetermined detector.

As above, if, in respective production processes, the information presenting substance associated with the information concerning the production process are added sequentially and dispersed to and in the thermoplastic plastic, even after the thermoplastic plastic is distributed in a market etc. in any given form, since the information concerning the production processes is present in the thermoplastic plastic itself, the information concerning the production process can be grasped easily.

Moreover, if the information presenting substance is added sequentially and dispersed to and in the thermoplastic plastic in respective production processes, and correspondence between the information concerning the production process and information concerning the information presenting substance associated with the information concerning production process is registered in a predetermined information management device and managed in an integrated manner, in this example, information concerning respective production processes in each thermoplastic plastic at the information management device of any thermoplastic plastic among the resin materials provided by the resin manufacture makers A company and B company, the master batches provided by the master batch manufacture makers C company and D company, and the molded product provided by the molding and processing maker E company, can also be obtained by specifying the type and the quantity of the information presenting substance contained therein.

Consequently, for example, even if search for cause when a problem in quality is occurred, separation for recycling, or determination whether products are genuine products produced by a normal producer or not, is required after the distribution of products, these purposes can be attained easily.

<Information Management System>

Next, referring to drawings, an information management system with respect to the thermoplastic plastic added with such an information presenting substance will be described.

FIG. 1 is a view explaining the entire configuration of an information management system. As shown in FIG. 1, the information management system 10 includes producer terminals 20 used by producers who perform respective production processes of thermoplastic plastics with sharing them, detectors 30 used by users who require information etc. concerning the production process of the thermoplastic plastic, and an information management device 50 having a function as a server controlling an information management system 10 which can transmit/receive information via the producer terminals 20, the detectors 30, and a network circuit 40 such as Internet.

<Producer Terminal>

The producer terminals 20 are used by producers who perform respective production processes with sharing them, and have functions of transmitting/receiving information concerning the production processes and information concerning information presenting substances between themselves and the information management device 50.

Each of the producer terminals 20 includes a computer etc. including storage means such as CPU, RAM, ROM, or a hard disk drive, an information-and-telecommunications equipment, an external input-output device, and the like, and an information processing function of transmitting/receiving various pieces of information between itself and the information management device 50 is constructed on the computer.

Information concerning respective production processes is input in respective producer terminals 20 by respective producers, and in the producer terminals 20, a processing that transmits the information to the information management device 50 to register it, is performed. Moreover, when respective production processes are performed, the producer terminals 20 are adapted to receive information concerning the information presenting substance to be added to thermoplastic plastics in respective production processes from the information management device 50 and to report it to the producers.

One type or plurality types of information presenting substances to be added to thermoplastic plastics are provided to respective producers in advance, separately, and production processes are performed by adding a designated type and amount of information presenting substance to the thermoplastic plastics when they are practically produced.

<Detector>

The detectors 30 are used by users requiring information concerning the production process of a thermoplastic plastic and have functions of detecting fluorescence spectrum radiated by an information presenting substance 91 from the thermoplastic plastic 90, which is a target object of information detection.

As those users who requiring information concerning production processes, those who require for specifying a genuine producer concerning a final product, recycling manufactures who require information of composition (additive) of a final product when recycling it, or producers who require information concerning a material of thermoplastic plastic sent from a upstream process and the like, can be included, and they are not limited in particular.

As hardware, each of the detectors 30 includes a computer including memory means such as CPU, RAM, ROM, or a hard disk drive, an information-and-telecommunications equipment, an external input-output device, and the like, and information processing functions of such as detecting a fluorescence spectrum from thermoplastic plastic and transmitting/receiving various pieces of information between itself and the information management device 50 are constructed on the computer.

The detector 30 includes fluorescence spectrum detecting means for detecting a fluorescence spectrum radiated from the information presenting substance 91 as a target object fluorescence spectrum corresponding when a target object (thermoplastic plastic) is irradiated with an electromagnetic wave in a predetermined wavelength range. The fluorescence spectrum detecting means include an excitation light source for emitting an electromagnetic wave (excited light) in a predetermined wavelength range, a condensing optical system for condensing the excited light to a site of the target object (thermoplastic plastic) 90, in which the information presenting substance 91 is contained, a receiving optical system for receiving fluorescence radiated by the information presenting substance 91 when it irradiated with the excited light, and a spectroscope for subjecting the fluorescence guided to the receiving optical system to a spectroscopic processing.

The detector 30 is adapted to transmit information concerning the fluorescence spectrum, detected from thermoplastic plastic, such as the wave-form thereof, to the information management device 50, receive the information concerning a production process specified by the information management device 50, and output it to users.

Figure 2:
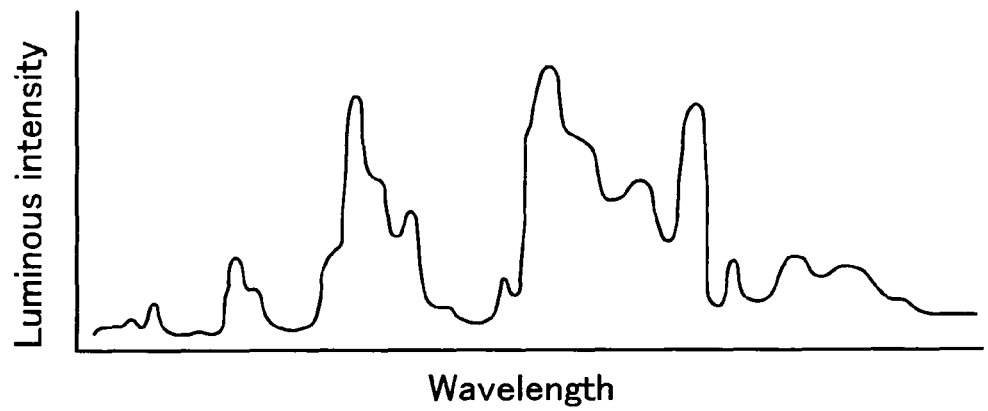
FIG. 2 is an example of the wave-form of a fluorescent spectrum detected from a certain target object.

FIG. 2 is an example of the wave-form of the target-object-fluorescence spectrum detected from a certain target object (thermoplastic plastic) 90 by the detector 30. One type or a plurality types of information presenting substances 91 are added to the target object 90, and when a plurality types of information presenting substances 91 are added, the target object-fluorescence spectrum detected from the target object 90 is superposition of the fluorescence spectra presented by respective information presenting substances 91 (individual fluorescence spectrum).

<Information Management Device 50>

The information management device 50 is managed by an operator operating the information management system 10 and has a function of a server controlling the information management system 10.

As hardware, the information management device 50 includes a computer including memory means such as CPU, RAM, ROM, or a hard disk drive, an information-and-telecommunications equipment, and an external input-output device etc, and information processing functions of such as managing information concerning respective production processes, identifying the fluorescent spectrum detected from thermoplastic plastic, which is the target object to be identified, and transmitting/receiving various pieces of information between itself and each of the producer terminals 20 and between itself and each of the detectors 30 are constructed on the computer. Moreover, the information management device 50 may be constructed by distributing a plurality of computers.

As functions, the information management device 50 includes information presenting substance storage means 51, production process information storage means 52, production-process-information registering means 53, fluorescent-spectrum analyzing means 54, information retrieving means 55, and transmitting/receiving means 56.

Figure 3:
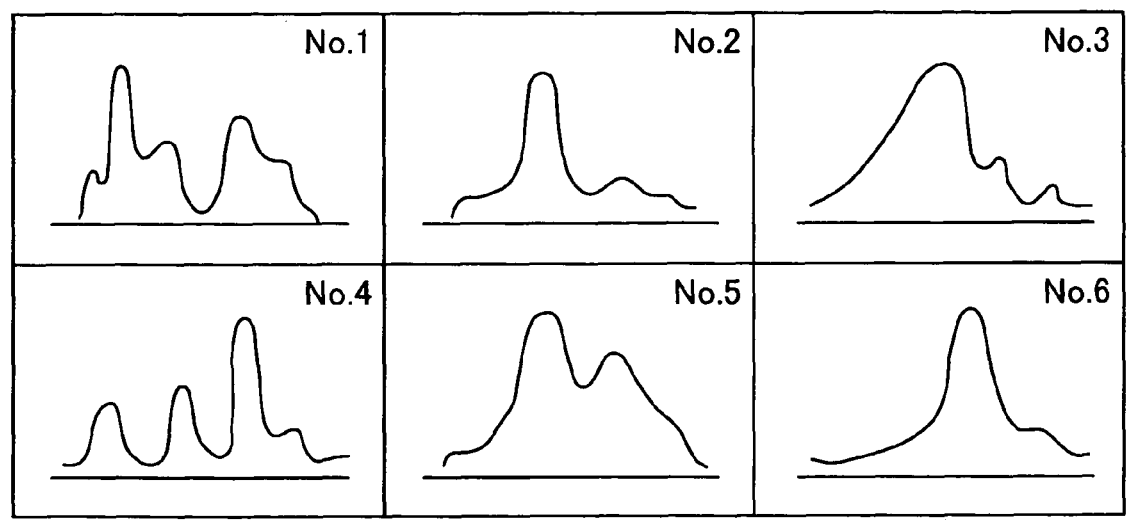
FIG. 3 is an example of the wave-form of a fluorescent spectrum of a genuine information presenting substance, memorized in advance.

The information presenting substance storage means 51 has a function of memorizing fluorescent spectra respectively radiated by limited types of genuine information presenting substances selected in advance when they are irradiated with an electromagnetic wave in a specified wavelength range. FIG. 3 is a view of examples of the individual fluorescent spectrum of the genuine information presenting substances stored in the information presenting substance storage means 51. In this example, six types of genuine information presenting substances No. 1 to No. 6 are selected in advance.

The production process information storage means 52 has a function of memorizing the information concerning respective production processes of thermoplastic plastics while associating it with the information concerning a specified information presenting substance. As described in the above-mentioned example, the information concerning respective production processes may include various pieces of information depending on stages etc. of the production processes.

The production-process-information registering means 53 has a function of registering the information concerning respective production processes performed by respective producers to the production process information storage means

52. The registering processing is desirable to be performed every time when the information to be built in the thermoplastic plastic concerning respective production processes in production processes performed by respective producers. For example, the manufacture time is distinguished per a month; it is desirable for the production period to be registered as a new production process.

Specifically, registering processing is performed in such a way where producers transmit information concerning a new production process together with requirement of registration from respective producer terminals 20 to the production-process-information registering means 53, and the production-process-information registering means 53 sets and registers the information concerning information presenting substance to be associated with the information concerning the new production process accordingly and informs the information concerning the information presenting substance to be added and dispersed to and in thermoplastic plastics in the new production process to producers via producer terminals 20.

The fluorescent-spectrum analyzing means 54 has a function of analyzing the information concerning the information presenting substance from the information concerning the fluorescence spectrum detected from the thermoplastic plastic 90, which is an object to be identified of the detector 30. As the information concerning the information presenting substance, for example, combination of the type and the quantity of the information presenting substance contained in the thermoplastic plastic 90 can be included.

Here, specifically, the fluorescence spectrum analyzing means 54 is constructed so as to specify the combination of the type and the quantity of the information presenting substance contained in the thermoplastic plastic, which is an object to be identified, by combining fluorescence spectra radiated by the limited types of genuine information presenting substances memorized in the information presenting substance storage means 51 in advance, and thereby recreating the fluorescent spectrum detected by the detector 30.

The recreation is performed by retrieving such a combination of fluorescence spectra from genuine information presenting substances that coincides with the fluorescence spectrum detected from the target object, in the whole of a predetermined wavelength range. As the predetermined wavelength range, any wavelength range where a part or entire of the feature of the individual fluorescence spectrum appear, may be arbitrarily set in advance. Moreover, the case of coincidence of spectrum includes the case where the difference between spectra to be compared is within a predetermined allowable range considering the effect of noises etc., or the like.

The recreation may be performed by sequentially confirming limited types of combinations, or also by using an arbitrary effective retrieving algorithm. For example, approaches such as further limiting the retrieving range by specifying information presenting substances, which should be surely contained in the target object 90 if it is a genuine product, from the detected target-object-fluorescence-spectra, and from the detected target-object-fluorescence-spectra preferentially retrieving the combination between information presenting substances having high possibility to be contained can be used.

In this way, in the information management system 10, by selecting limited types of information presenting substances as genuine information presenting substances and combining them to recreate the fluorescence spectrum detected from the target object to be identified, even when false products presenting fluorescence spectrum similar to those of genuine products are produced by a third person, the false product can be identified by finding out the difference in fluorescence spectrum between itself and the combination of genuine information presenting substances in whole of a predetermined wavelength range, thereby high reliability can also be ensured in determination whether a product is a genuine product or not.

The information retrieving means 55 has a function of specifying information concerning production processes associated with the information presenting substances by retrieving the production process information storage means 52 based on the information concerning the information presenting substances in the thermoplastic plastic 90 (combination of genuine information presenting substances), which are the target object to be identified, obtained by the fluorescence-spectrum analyzing means 54.

The information outputting means 56 has a function of outputting (transmitting) the specified information concerning the production process to the detector 30 used by a user.

According to the information management system 10 including such an information management device 50, since the information concerning the types and fluorescence spectra of the genuine information presenting substances, and the information concerning respective production processes are managed in an integrated manner in the information management device 50 separated from respective manufacturing sites where the thermoplastic plastics 90, which are target objects to be identified, are produced, and an identifying site where information concerning production processes is tried to be taken out from the thermoplastic plastics 90, consequently, confidentiality of the information concerning the genuine information presenting substances can be enhanced and the possibility of false products can be reduced.

Moreover, since a specifying processing of information concerning production processes incorporated in the thermoplastic plastics 90 is performed at the side of the information management device 50, performance burden required for respective producer terminals 20 and detectors 30 can be reduced, and these devices 20 and 30 can be small and portable.

<Flows of Respective Production Processes>

Figure 4:
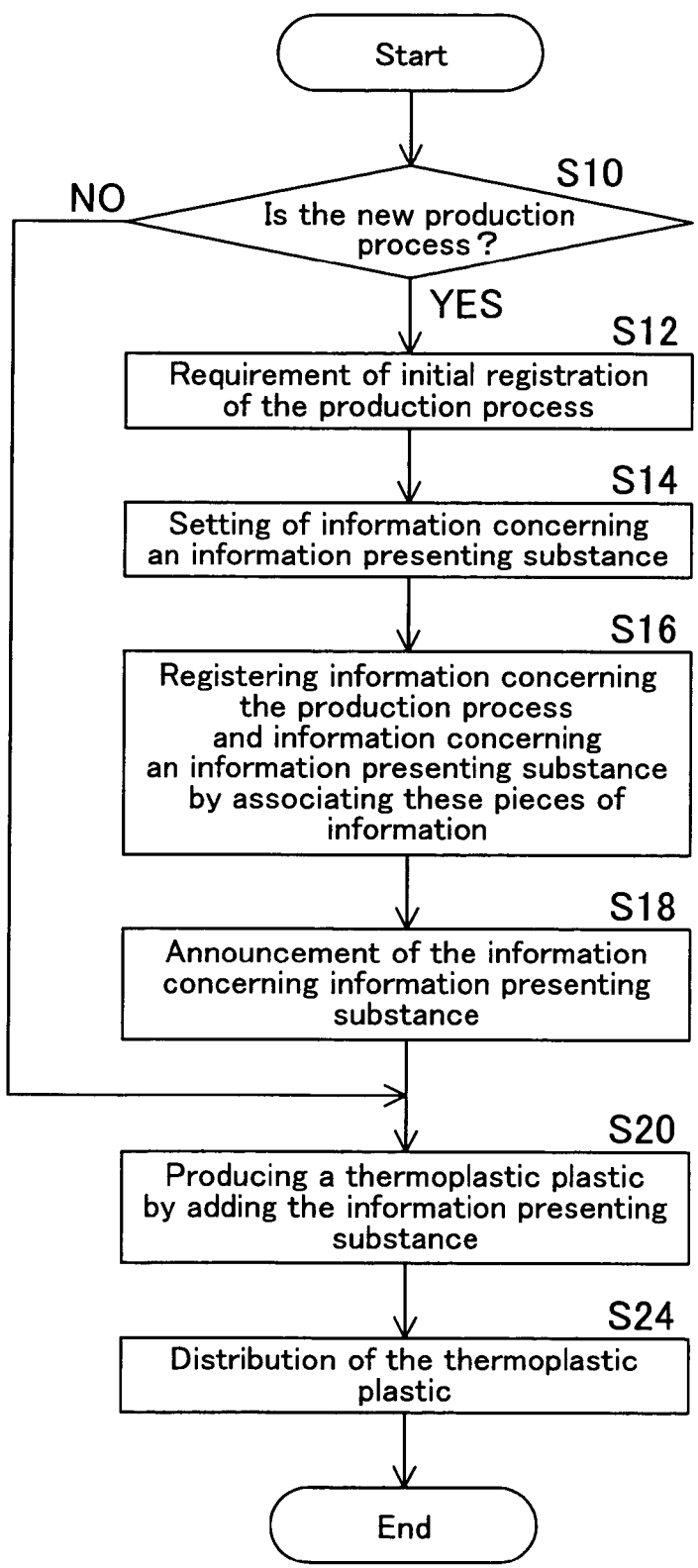
FIG. 4 is a flowchart showing a series of flows from the production to the distribution of a thermoplastic plastic.

Next, including the information management processing in the information management system 10, a series of flows from the production of thermoplastic plastics, which are the objects to be managed by the system 10 to the distribution thereof, will be described with reference to the flow chart of FIG. 4.

The series of flows represent a case where, using a thermoplastic plastic or another material produced in an upstream process as the material in the production process, a certain producer produces the thermoplastic plastic as an output in the production process, and are sequentially repeated to the thermoplastic plastic in the plurality of production processes thereof.

In the production process, whether the production process to be performed is a new production process or not is determined by the producer (S10), and if the production process is a new production process (YES at S10), a registering processing of information concerning the production process will be performed.

In the registering processing of information concerning the production process, the information concerning the production process is input in the producer terminal 20 by the producer, and, in order to register it, a requirement for initial registration of the production process is sent from the producer terminal 20 to the information management device 50 (S12).

In the information management device 50 received the requirement for initial registration, information concerning an information presenting substance to be associated with the information concerning the new production process is set (S14), and registered in the production process information storage means 52 by associating the information concerning the production process with the information concerning an information presenting substance (S16), and the information concerning an information presenting substance thus registered is sent to the producer terminal 20 to be announced to the producer, as information concerning the information presenting substance to be added to the thermoplastic plastic in the production process (S18).

The announced producer produces thermoplastic plastic by adding the type of and the quantity of information presenting substance, which is designated by the announcement (S20).

Moreover, if the production process to be performed is not a new production process (NO at S10), the producer will produce the thermoplastic plastic by adding the information presenting substance the same as that added in the same production process performed in the past (S20).

The thermoplastic plastic thus produced is distributed to producers at the side of downstream as an intermediate product (or an intermediate material) in a series of production processes, or provided to a market as a final product and distributed to consuming public etc. (S24), and the production process will be finished.

Moreover, even when a new production process is not performed, it is desirable to transmit information concerning the production process to be performed from the producer terminal 20 to the information management device 50, and then to answer the information concerning the information presenting substance already associated with the information concerning the production process from the information management device 50 to the producer terminal 20, so that the producer can confirm the information presenting substance to be added.

<Flow of Information Identifying Processing>

Figure 5:
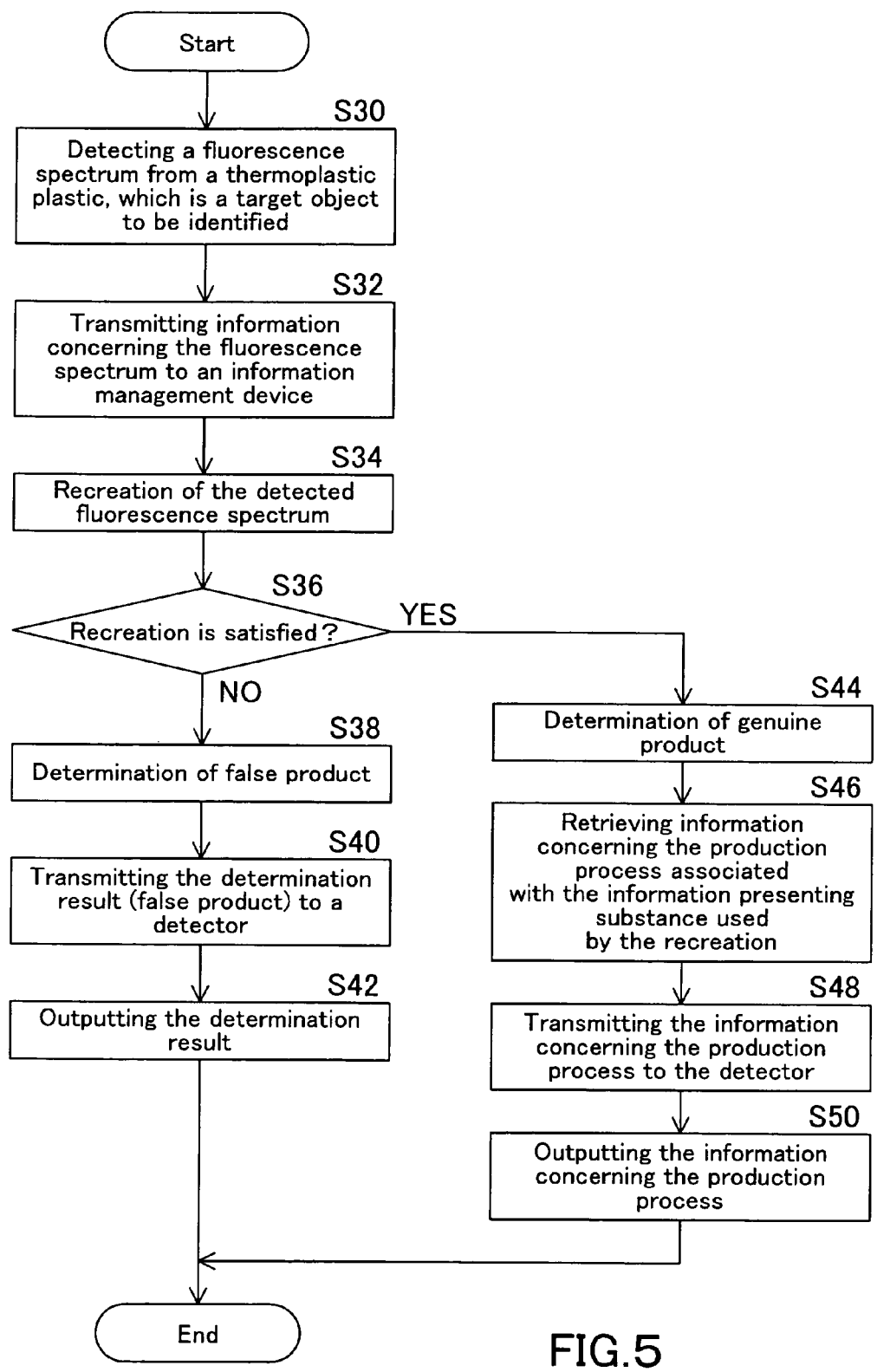
FIG. 5 is a flowchart showing a series of flows of identification processing of incorporated information concerning a production process from the distributed thermoplastic plastic.

Next, including the information management processing in the information management system 10, a series of flows for identifying information concerning the production process incorporated in distributed thermoplastic plastic from the distributed thermoplastic plastic, will be described with reference to the flowchart in FIG. 5.

Each of the series of flows is performed respectively, if required, in users etc. of the final product and in respective producers etc. in respective stages of production.

In the information identifying processing, at the detector 30, a fluorescence spectrum is detected from the thermoplastic plastic, which is the target object to be identified, by a user presenting near the thermoplastic plastic, which is the target object to be identified (S30), the information concerning the detected fluorescence spectrum is sent from the detector 30 to the information management device 50 (S32).

In the information management device 50 received the information, recreation of the fluorescence spectrum detected from the thermoplastic plastic is tried by combining fluorescence spectra of genuine information presenting substances using the fluorescence-spectrum analyzing means 54 (S34), and if the recreation cannot be performed (NO at S36), the thermoplastic plastic is determined as a false product, which is not the target object to be managed in the system 10 (S38), and the determination result (false product) is sent to the detector 30 (S40). In the detector 30 received the result, the determination result (false product) is announced to users by displaying and outputting it (S42), and the series of identifying processings will be finished.

Meanwhile, if the recreation of fluorescence spectrum of the thermoplastic plastic, which is the target object to be identified, can be performed by combining the fluorescence spectra of the genuine information presenting substances (YES at S36), the thermoplastic plastic 90 is determined as a genuine product (S44), the information concerning the production process associated with the type and the quantity of the information presenting substance used in the recreation (information concerning the information presenting substance) is retrieved from the production process information storage means 52 (S46), and the retrieved information is sent to the detector 30 (S48). In the detector 30 received the information, the information is displayed and output as information concerning the production process of the thermoplastic plastic (S50), and the series of information identifying processings are finished.

Another Embodiment

Although the present invention is described based on an embodiment, the present invention is not limited to the above-mentioned embodiment, rather it may be constructed as follows.

(1) In the above-mentioned embodiment, the information concerning the production process is input by the producer terminals 20, and the information concerning information presenting substance from the thermoplastic plastic 90 (fluorescence spectrum) is detected by the detectors 30, however, one or both of these processings may be performed by the information management device 50.

(2) The transmitting/receiving processing of various pieces of information between the producer terminals 20 and the information management device 50 and between the detectors 30 and the information management device 50 may be performed using coded information which can be encoded by both sides.

(3) Although in the above-mentioned embodiment, as information to be incorporated in the thermoplastic plastic by an information presenting substance, only the information concerning the production process is included, other information may also be carried by the information presenting substance so as to be incorporated in the thermoplastic plastic. As such information other than production configuration, for example, in case of a bank card or a cash card, as information concerning it, information such as information concerning a user or an identification number is included. Moreover, in case of a check, a document of value, or a bank bill, as information concerning it, information such as an identification number or an identification mark is included. Moreover, in case of a label etc. appended to a food, as information concerning it, information such as a place of production or a production date of the food, is included. Moreover, in case of an identification card for hospital, information such as chart information or drug information is included. Moreover, in case of an identification card etc. for resident management, information such as information described in a resident card or a certificate of a seal impression is included.

(4) In the fluorescence spectra etc. detected from the thermoplastic plastic, the time-damping property thereof etc. may be included.

(5) Although in the above-mentioned embodiment, in each production process, the information presenting substance to be added to the thermoplastic plastic is associated with the information concerning the production process, an information presenting substance associated with the information concerning a production process at the side of the upstream or the downstream of the production process may be added to the thermoplastic plastic.

(6) Although in the above-mentioned embodiment, only information presenting substance is adapted to carry the information concerning the production process, various pieces of information may be incorporated in the thermoplastic plastic using combination of the information presenting substance and color information presented by the thermoplastic plastic by causing a substance coloring the appearance of the thermoplastic plastic such as pigment, which is added and dispersed to and in the thermoplastic plastic similar to information presenting substances, to carry information. In this case, by the detector 30, fluorescence spectrum due to the information presenting substance is read out from the thermoplastic plastic as an target object to be identified, and by predetermined color detecting means or by means of viewing by a user, color information of the thermoplastic plastic is read out, both pieces of information concerning the fluorescence spectrum and concerning the color of the thermoplastic plastic are sent to the information management device 50, and information concerning production process memorized in the information management device 50 while being associated with the combination of these pieces of information is retrieved so that the information concerning production process can be output. In this manner, if the color information of the thermoplastic plastic is also used, the quantity of information to be carried by the thermoplastic plastic can be increased.

Moreover, although the information to be associated with the color presented in the appearance of the thermoplastic plastic may be the information of the production process itself, it may also be the information concerning a thermoplastic-plastic product.

Further, the types of the thermoplastic plastic, which is the target object to be identified, can be increased by combining the color information of the thermoplastic plastic to the information of the information presenting substance.

For example, when a thermoplastic-plastic product subjected to same processes such as a polymerization process and a granulating process of a thermoplastic plastic resin, a production process of additive concentrate, and a production process and molding process of a composition is sold to a plurality of distributors, it is possible to further add and incorporate the information of a distributor to and in the thermoplastic-plastic product by changing the color of the thermoplastic-plastic product with respect to each distributor.

Moreover, although addition of a substance coloring the thermoplastic plastic may be performed in any one of production processes involving fusion, among others, the production process of an additive concentrated composition and the production process of a thermoplastic-plastic composition are preferable.

This application is to claim a priority of Japanese Patent Application No. 2004-139652, filed on May 10, 2005, and disclosure of which is incorporated herein in its entirety for form a part of this application.

The terms and descriptions used here have been used for explaining the embodiments according to the present invention; thereby the present invention is not limited to these. Thus, the present invention allows any designing change within the scope of the claims as long as it does not depart from the spirit of the present invention.

The invention claimed is:

1. A method for producing a thermoplastic plastic comprising:
   performing a plurality of production processes on a batch of the thermoplastic plastic, wherein each of the production processes includes fusion of the thermoplastic plastic, adding an information presenting substance to the thermoplastic plastic, and dispersing the information presenting substance therein,
   wherein the information presenting substance added in each production process is associated with information concerning that production process and radiates fluorescence upon an irradiation of an electromagnetic wave in a specified wavelength region.

2. The method for producing a thermoplastic plastic as recited in claim 1, wherein the plurality of production processes are performed by a plurality of producers.

3. The method for producing a thermoplastic plastic as recited in claim 1, wherein each information presenting substance is an inorganic compound including lanthanoid elements.

4. The method for producing a thermoplastic plastic as recited in claim 1, wherein the information concerning each of the production process associated with the information presenting substance includes at least any one of information concerning a base material of the thermoplastic plastic, information concerning additives in each of the production process, information concerning producers performing each of the production process and information concerning a product obtained from the thermoplastic plastic.

5. A thermoplastic plastic to which an information presenting substance is added sequentially and dispersed therein in each of a plurality of production processes including fusion of the thermoplastic plastic,
   wherein the information presenting substance is associated with information concerning each of the production process and radiates fluorescence upon an irradiation of an electromagnetic wave in a specified wavelength region.

6. An information management device of a thermoplastic plastic for managing information concerning a plurality of production processes including fusion of the thermoplastic plastic,
   wherein the device determine information concerning each of the production processes from the fluorescence, upon irradiation of an electromagnetic wave in a specified wavelength region, from information presenting substances added to the thermoplastic plastic and dispersed therein in each of the production processes, and the device memorize said information.

7. The information management device of a thermoplastic plastic as recited in claim 6, wherein information specifying the information presenting substance to be added in each of the production process is sent to a terminal used by a producer performing each of the production process through network circuit.

8. The information management device of a thermoplastic plastic as recited in claim 6, wherein the device obtains information concerning fluorescence spectrum as information concerning the information presenting substance from a detector for detecting the fluorescence spectrum and outputs information concerning each of the production process of the thermoplastic plastic associated with the information concerning the information presenting substance, and
   wherein the detector irradiates a predetermined electromagnetic wave to the thermoplastic plastic and detects the fluorescence spectrum radiated by the information presenting substance.

9. The method for producing a thermoplastic plastic as recited in claim 2, wherein the information presenting substance is an inorganic compound including lanthanoid elements.

10. The method for producing a thermoplastic plastic as recited in claim 2, wherein the information concerning each of the production process associated with the information presenting substance includes at least any one of information concerning a base material of the thermoplastic plastic, information concerning additives in each of the production process, information concerning producers performing each of the production process and information concerning a product obtained from the thermoplastic plastic.

11. The method for producing a thermoplastic plastic as recited in claim 3, wherein the information concerning each of the production process associated with the information presenting substance includes at least any one of information concerning a base material of the thermoplastic plastic, information concerning additives in each of the production process, information concerning producers performing each of the production process and information concerning a product obtained from the thermoplastic plastic.

12. The method for producing a thermoplastic plastic as recited in claim 9, wherein the information concerning each of the production process associated with the information presenting substance includes at least any one of information concerning a base material of the thermoplastic plastic, information concerning additives in each of the production process, information concerning producers performing each of the production process and information concerning a product obtained from the thermoplastic plastic.

13. The information management device of a thermoplastic plastic as recited in claim 7, wherein the device obtains information concerning fluorescence spectrum as information concerning the information presenting substance from a detector for detecting the fluorescence spectrum and outputs information concerning each of the production process of the thermoplastic plastic associated with the information concerning the information presenting substance, and wherein the detector irradiates a predetermined electromagnetic wave to the thermoplastic plastic and detects the fluorescence spectrum radiated by the information presenting substance.

* * * * *